United States Patent
Schulze

(10) Patent No.: US 6,304,514 B1
(45) Date of Patent: Oct. 16, 2001

(54) ULTRASONIC MEASURING DEVICE WITH TRANSMITTERS AND RECEIVERS FOR LOCATING THE GEOMETRIC POSITION OF THE BORDER BETWEEN A FIRST AND SECOND MATERIAL FROM A REFERENCE LOCATION

(75) Inventor: Torsten Schulze, Bad Oeynhausen (DE)

(73) Assignee: Theyson GmbH, Langenhagen (DE)

( * ) Notice: Subject to any disclaimer, the term of this patent is extended or adjusted under 35 U.S.C. 154(b) by 0 days.

(21) Appl. No.: 09/508,872
(22) PCT Filed: Sep. 12, 1998
(86) PCT No.: PCT/EP98/05819
§ 371 Date: Mar. 17, 2000
§ 102(e) Date: Mar. 17, 2000
(87) PCT Pub. No.: WO99/15855
PCT Pub. Date: Apr. 1, 1999

(30) Foreign Application Priority Data

Sep. 20, 1997 (DE) .............................................. 197 41 586

(51) Int. Cl.$^7$ ....................................................... G01S 15/00
(52) U.S. Cl. ............................................................. 367/98
(58) Field of Search ................................. 367/87, 98, 99, 367/100; 73/609, 614, 615, 616

(56) References Cited

FOREIGN PATENT DOCUMENTS

19526014-A * 1/1997 (DE) .

* cited by examiner

Primary Examiner—Daniel T. Pihulic

(57) ABSTRACT

The invention relates to an ultrasonic measuring apparatus for determining the geometrical position of a boundary between two materials in a first material from a reference place, more particularly for wall thickness or fault testing. To enable even very thin-walled materials to be measured, the measuring apparatus isolates the reflected ultrasonic signals from the ultrasonic mixed signal received by the receiver, which consists of the ultrasonic signal reflected at the boundary to the first material and the ultrasonic signal reflected at the boundary to the second material, so that the time of impingement of the reflected signal is clearly determined for the determination of propagation time.

1 Claim, 1 Drawing Sheet

ULTRASONIC MEASURING DEVICE WITH TRANSMITTERS AND RECEIVERS FOR LOCATING THE GEOMETRIC POSITION OF THE BORDER BETWEEN A FIRST AND SECOND MATERIAL FROM A REFERENCE LOCATION

BACKGROUND OF THE INVENTION

The invention relates to an ultrasonic measuring apparatus with transmitter and receiver for locating the geometrical position of the boundary between a first and a second material by measuring and comparing the propagation times required for return to the receiver by an ultrasonic signal emitted by the transmitter and reflected at the boundary to the first material and an ultrasonic signal reflected at the boundary to the second material.

Ultrasonic measuring apparatuses of the kind specified are known (DE 195 26 014 A1). Reliable results concerning the distance of boundary surfaces are obtained from the speed of propagation of an ultrasonic signal in the first material. Such ultrasonic measuring apparatuses are used for measuring wall thicknesses. Measurement is problem-free if the ultrasonic signal reflected at the boundary to the first material has already decayed when the signal reflected at the boundary to the second material reaches the receiver again. This precondition is met in the case of materials in which the boundary to the first material is far enough away from the boundary to the second material. In these cases the individual reflected signals can be selected in dependence on the sequence of their impingement and assigned to the boundary layers. This prior art does not solve the problem that the signal received is a mixed signal which, due to the small thickness of the individual layers, is composed of the signals reflected at the different layers. Such a signal cannot be readily analysed for layer thickness measurement.

For measuring the thickness of multilayer plastics pipes, etc., a process is also known (DE 195 34 503 A1) which is based not on the measurement of propagation time, but on the measurement of the amplitudes of the ultrasonic signal at resonance frequency.

Lastly, an ultrasonic measuring process is known (DE 34 18 486 C1) which is used not for measuring the thickness of thin layers/walls, but for eliminating faults close to the rear wall. This is done by the reflected signal being compared with the signal sample which is characteristic of the course of the rear wall echo up to its maximum extreme value of amplitude.

It is an object of the invention to provide an ultrasonic measuring apparatus also suitable for locating the geometrical position of a boundary between two materials which is situated very close to a place of reference, for example, another boundary between two materials, so that the measuring apparatus is also in a position to determine the thickness of very thin-walled materials.

SUMMARY OF THE INVENTION

This problem is solved with an ultrasonic measuring apparatus of the kind specified by the features that from the ultrasonic signal received by the receiver the ultrasonic signal reflected at the boundary to the second material is isolated by forming the difference between the ultrasonic signal received and a reference signal corresponding to the ultrasonic signal reflected at the boundary to the first material, and the propagation time of the ultrasonic signal through the first material is determined from the time up to the first rise in the reference signal and the time up to the first rise in the received ultrasonic signal.

According to the invention, therefore, the ultrasonic signal reflected at the boundary to the second material is filtered out of the ultrasonic signal received by the receiver, which is composed of the ultrasonic signals reflected at the two boundaries, to the first material and from the first-to the second material. As in the prior art measuring apparatus, for propagation time measurement two clear signals are then available, the signal reflected at the boundary to the first material and the signal reflected at the boundary to the second material.

The term "boundary" is taken to mean not only a distinctly contoured boundary between two materials but also, for example, changes in homogeneity in a material which cause a reflection of the ultrasonic signal. The isolated signal provides information not only concerning the location of the boundary from the first to the second substance in relation to a place of reference, for example, the thickness of the first material, but also information concerning the material itself, on the basis of the amplitude of the reflected signal. The principle of propagation time measurement according to the invention can be used not only with a single material, but also with laminated materials. In the case of a material consisting of two layers, a further signal reflected at the boundary from the second to the third material is obtained in addition to the signal reflected at the boundary from the first to the second material. The principle of isolating this signal reflected at the boundary from the second to the third material is the same as that of insulating the signal reflected from the boundary from the first to the second material.

Figure 1:
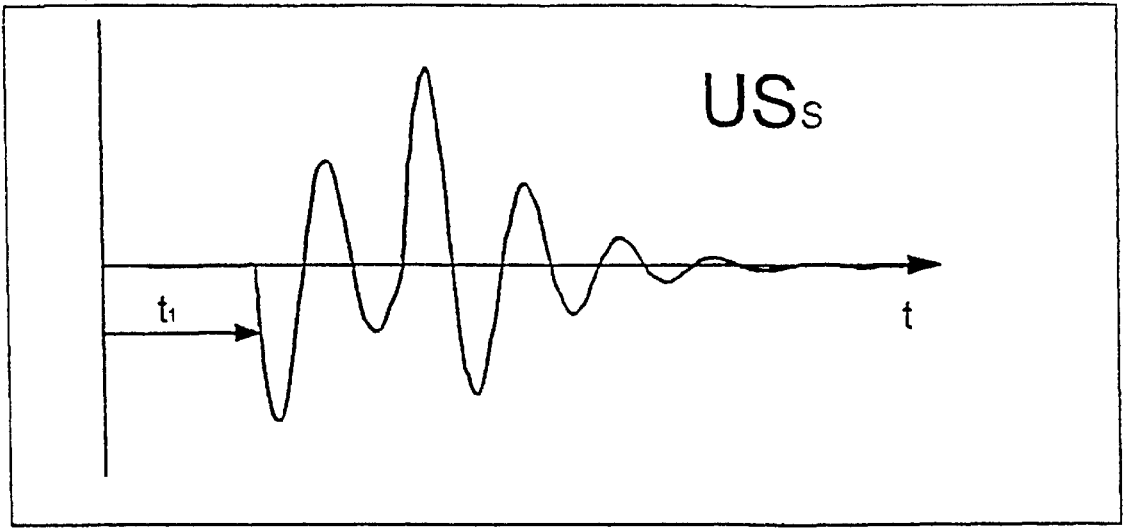
FIG. 1 is a chart of a received signal $US_S$.
Figure 2:
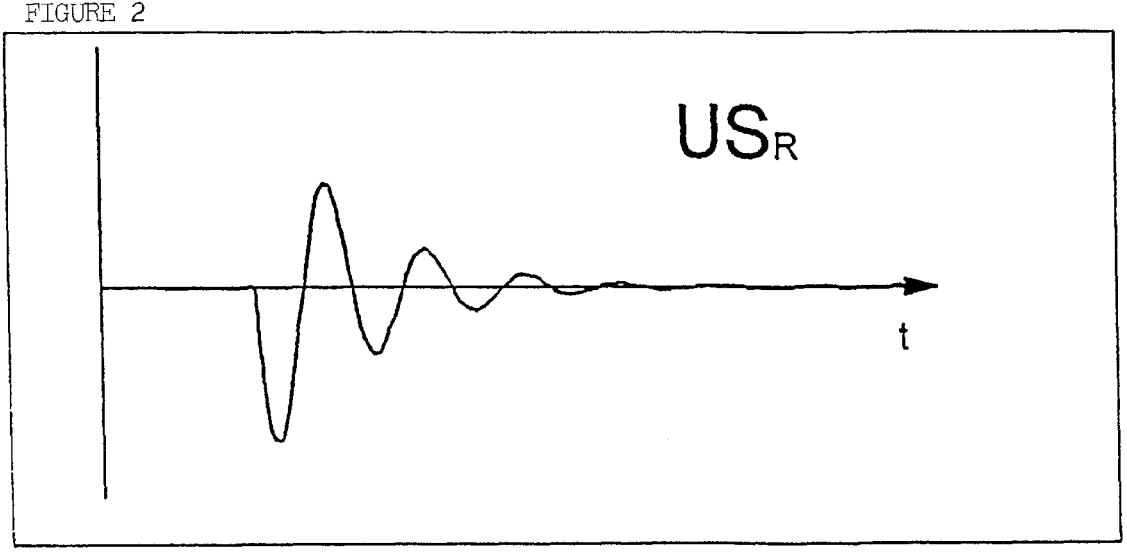
FIG. 2 is a chart of a reference signal $US_R$.
Figure 3:
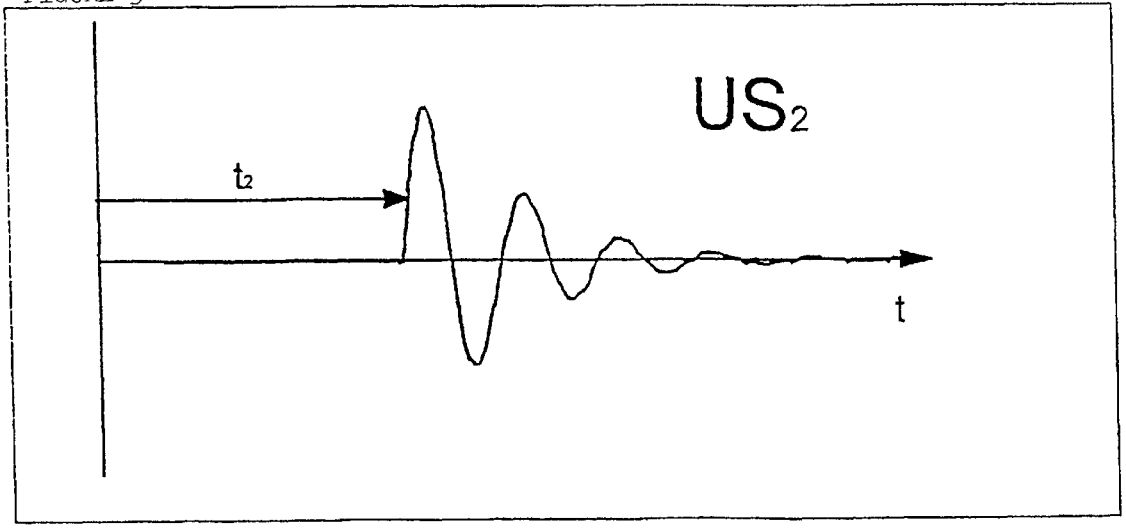
FIG. 3 is a chart of a composite signal $US_2$.

The invention will now be explained in greater detail with reference to ultrasonic signals.

DETAILED DESCRIPTION OF THE DRAWINGS

Just like the conventional measuring apparatuses for measuring propagation timed by ultrasonics, the measuring apparatus according to the invention comprises a transmitter, a receiver, and ultrasonic coupling elements to be coupled to the material to be measured. The transmitter introduces into the first material an ultrasonic signal which is reflected at the first boundary (place of entry) of the material to be measured. However, the signal also passes as far as the second boundary of the material to be measured, where it is again reflected and from where it returns to the starting point.

One special feature of the measuring apparatus according to the invention is that the received signal $US_S$ is processed twice. For this purpose the time $t_1$ to the first rise in the ultrasonic signal is determined on entry into the first material. Then the signal reflected at the boundary to the second material is isolated from the residual signal reflected at the boundary to the first material and the signal reflected at the boundary to the second material. This is done by the received signal $US_S$ being overlayered with a reference signal $US_R$ which corresponds to an ultrasonic signal reflected at the first boundary. The overlayering, namely a differentiation, produces a signal $US_2$ which corresponds to the signal reflected at the second boundary. The time $t_2$ is marked by the first rise in the signal $US_2$ reflected at the boundary to the second material. From the times $t_1$ and $t_2$ it is possible to determine the propagation time $\Delta_t$ for the ultrasonic signal in the material to be measured and therefore, if the speed of propagation of the ultrasonic signal in said material is known, the geometrical location of the boundary, more particularly the thickness of the material to be measured, but also faulty places or changes in homogeneity.

What is claimed is:

1. An ultrasonic measuring apparatus with transmitter and receiver for locating the geometrical position of the boundary between a first and a second material by measuring and comparing the propagation times required for return to the receiver by an ultrasonic signal ($US_R$) emitted by the transmitter and reflected at the boundary to the first material and an ultrasonic signal ($US_2$) reflected at the boundary to the second material, characterized in that from the ultrasonic signal ($US_S$) received by the receiver the ultrasonic signal ($US_2$) reflected at the boundary to the second material is isolated by forming the difference between the ultrasonic signal ($US_S$) received and a reference signal ($US_2$) corresponding to the ultrasonic signal ($US_R$) reflected at the boundary to the first material, and the propagation time of the ultrasonic signal through the first material is determined from the time ($t_2$) up to the first rise in the reference signal ($US_2$) and the time ($t_1$) up to the first rise in the received ultrasonic signal ($US_S$).

* * * * *